United States Patent [19]

Baran et al.

[11] Patent Number: 4,499,289
[45] Date of Patent: Feb. 12, 1985

[54] OCTAHYDRONAPTHALENES

[75] Inventors: John S. Baran, Winnetka; Chi-Dean Liang, Glenview, both of Ill.

[73] Assignee: G. D. Searle & Co., Skokie, Ill.

[21] Appl. No.: 549,534

[22] Filed: Nov. 7, 1983

Related U.S. Application Data

[63] Continuation-in-part of Ser. No. 446,546, Dec. 12, 1982, abandoned.

[51] Int. Cl.³ ............................................. C07D 309/30
[52] U.S. Cl. .................................................... 549/292
[58] Field of Search ......................................... 549/292

[56] References Cited

U.S. PATENT DOCUMENTS 3,983,140  9/1976  Endo et al. .......................... 549/292
4,282,155  8/1981  Smith et al. ......................... 549/292
4,450,171  5/1984  Hoffman et al. ..................... 549/292

Primary Examiner—Norma S. Milestone
Attorney, Agent, or Firm—John J. McDonnell

[57] ABSTRACT

The invention relates to octahydronapthalenes which are useful in antiatherosclerotic agents.

1 Claim, No Drawings

OCTAHYDRONAPTHALENES

This is a continuation-in-part of application Ser. No. 446,546 filed Dec. 12, 1982, now abandoned.

BACKGROUND OF THE INVENTION (a) Field of the Invention

The present invention provides novel compounds. In particular, this invention relates to novel octahydronaphthalenes of Formula XXVI.

The compounds of the present invention are useful as hypobetalipoproteinemic agents which are used to treat a mammal suffering from or susceptible to the development of an atherosclerotic disease.

Atherosclerosis in mammals is a disease characterized by the deposition of atherosclerotic plaque on arterial walls. Atherosclerosis exhibits many various forms and consequences. Typical consequences of atherosclerotic diseases include angina pectoris, mycardial infarction, stroke and transient cerebral ischemic attacks. Other forms of atherosclerotic diseases include certain peripheral vascular diseases and other ischemias (e.g., bowel and renal).

Medical science now recognizes that certain forms of atherosclerosis may be preventable or reversible. Agents capable of preventing or reversing atherosclerosis are characterized as exhibiting antiatherosclerotic activity. Since serum lipids have a recognized association with atherogenesis, an important class of antiatherosclerotic agents are those with serum lipid-modifying effects. Serum lipids implicated in atherogenesis include serum cholesterol, serum triglycerides, and serum lipoproteins.

With respect to serum lipoproteins, at least three different classes of these substances have been characterized; high-density lipoproteins (HDL's), low density lipoproteins (LDL's) and very low-density lipoproteins (VLDL's). HDL's are betalipoproteins. The control of LDL and VLDL levels (hypobetalipoproteinemic activity) is postulated to have a direct antiatherosclerotic effect. See Goodman and Gilman, *The Pharmacological Basis of Therapeutics*, fifth Ed. 744–752 (1975). The importance of lowering cholesterol levels may further be demonstrated by the availability of several commercial prescription products that are designed to lower cholesterol by several routes. See Physicians Desk Reference 1981, dextrothyroxine sodium pg. 898, clofibrate pg. 605, and cholestyramine pg. 1149. Several mechanisms of action have been described, for example, stimulation of the liver to increase catabolism and excresion of cholesterol, blocking the absorption of cholesterol in the intestine, and elimination by emulsification. The compounds of the present invention inhibit the production of cholesterol directly by interfering with HMG CoA reductase. This is beneficial in that serum liprotein levels of cholesterol are kept low without the need to eliminate excess cholesterol. The compounds of the invention are therefore also beneficial in cases of hypercholesterol production.

(b) Prior Art

The relationship between high blood cholesterol, atherosclerosis and medicament to control cholesterol are well known as described above. In addition it is known that 3-hydroxy-3-methylglutaryl-Coenzyme A reductase is the rate-limiting enzyme in the cholesterol synthetic pathway. Endo et al., described (U.S. Pat. Nos. 4,049,495 and 3,983,140) a fermentation product obtained by cultivation of a microorganism of the genus Penicillium, useful as an inhibitor in vivo of the biosythesis of cholesterol. Further, Monaghan, et. al. (U.S. Pat. No. 4,231,938), described certain lactones as well as their free hydroxy acids useful in the treatment of hypercholesteremia and hyperlipemia.

SUMMARY OF THE INVENTION

Accordingly it has been discovered that the compounds of present invention of the formula:

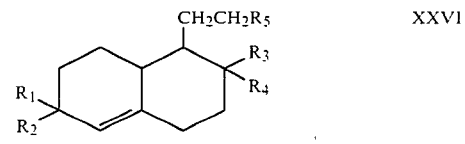

wherein $R_1$, $R_2$, $R_3$ and $R_4$ are hydrogen, alkyl of 1 to 6 atoms inclusive or fluorine, $R_1$, $R_2$, $R_3$ and $R_4$ each being the same or different.

Wherein $R_5$ is:

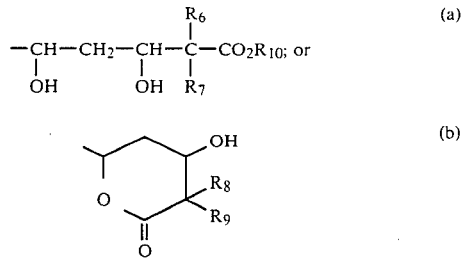

wherein $R_6$, $R_7$, $R_8$, $R_9$ and $R_{10}$ are hydrogen, alkyl of 1 to 6 carbon atoms, inclusive or fluorine, $R_6$, $R_7$, $R_8$ and $R_9$ each being the same or different and the pharmacologically acceptable salts are useful for their hypobetalipoproteinemic activity.

Examples of alkyl of 1 to 6 carbon atoms inclusive are methyl, ethyl, butyl, propyl, pentyl, hexyl and the isomeric forms thereof.

The test procedure used to determine hypobeta-lipoproteinemia is as follows:

Hepatic β-hydroxy-β-methylglutaryl-coenzyme A Reductase (HMG CoA reductase) inhibition is measured in the rat. Rats used are males weighing from 180–220 g pretreated with 2% diethylaminoethanolamine in diet using reversed lighting. 1 Millimolar final concentration of test compound is used in liver in vitro testing. Activity for each compound is reported as a percent inhibition based on control. A compound is considered active if it inhibits the conversion of $^{14}$C-Hydroxymethylglutaryl-CoA to $^{14}$C-mevalonolactone in the prescribed assay by 40% or more. If significant activity is observed, a titration will be done to determine potency and affinity for enzyme relative to substrate. HMG CoA reductase is the rate controlling enzyme in the synthesis of cholesterol. An agent which inhibits the enzymatic activity would be expected to reduce conversion of precursors to cholesterol. Therefore, an agent which inhibits this enzyme should be beneficial in the treatment of hyperlipoproteinemia with enhanced cholesterol biosynthesis.

The term "pharmaceutically acceptable salts" refers to cationic salts such as sodium potassium, calcium, magnesium, aluminum, ammonium, etc.

The mammals susceptible to the development of atherosclerotic diseases and the untoward consequences thereof are particularly those physically asymptomatic patients manifesting one or more risk factors known to predispose one to disease development. Such risk factors are high serum cholesterol and serum triglycerides, hypertension, obesity, diabetes, and genetic predisposition. Mammals manifesting two or more risk factors are deemed to be especially susceptible to atherosclerotic diseases. Accordingly, in using the compound of the invention for the instant purposes, an oral route of administration, either by conventional oral dosage forms or by mixture with food or feed, represents the preferred method of their systemic administration. Alternatively, however, these compounds may be administered by other convenient routes of administration whereby systemic activity is obtained. These other routes of administration would, accordingly, include rectal, vaginal, subcutaneous, intravenous, and like routes.

Liquid dosage forms for oral administration include pharmaceutically acceptable emulsions, solutions, suspension, syrups, and elixirs containing inert diluents commonly used in the art, such as water. Besides, such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions, or emulsions. Examples of non-aqueous solvents or vehicles are vegetable oils, such as olive oil, and injectable organic esters such as ethyl oleate. Such dosage forms may also contain adjuvants such as preserving, wetting, emulsifying, and dispersing agents. They may be sterilized, for example, by filtering through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as cocoa butter or a suppository wax.

Compositions for nasal or sublingual administration are also prepared with standard excipients well known in the art.

The compounds of the present invention are useful hypobetalipoproteinemic agents at dosages from 100 mg/kg to 2 g/kg daily preferably in divided dosages. The dosage of active ingredient in the compositions of this invention may be varied; however, it is necessary that the amount of the active ingredient shall be such that a suitable dosage form is obtained. The selected dosage depends upon the desired therapeutic effect, on the route of administration, and on the duration of the treatment.

The compounds of this invention are prepared from 3,4-dihydro-6-alkoxy-1(2H)-naphthalenes, Formula I, by the methods illustrated in the attached Charts A through C. Alkylation of I with an alkyl acetate, under strongly basic conditions in an inert organic solvent, affords substituted octahydronaphthalenes of Formula II. Preferred alkylating conditions employ ethyl acetate and lithium isopropylmethyl amide (prepared in situ by reaction of isopropylmethylamine and butyl lithium) in tetrahydrofuran. Catalytic hydrogenation of II removes the 1-hydroxyl group, giving compounds of Formula III. Typical hydrogenation conditions include hydrogen gas at about 60 psi, an alcoholic solvent, and a transition metal catalyst. Preferred conditions employ ethanol solutions of Formula II over palladium on carbon as catalyst. Esters of Formula III can further be converted to corresponding alcohols, Formula IV, by reduction with an active metal hydride, preferably lithium aluminum hydride, in an inert organic solvent, such as diethyl ether. Compounds of Formula V are prepared from Formula IV by partial reduction in ammonia using a dissolving alkali metal, such as lithium or sodium, preferably lithium. Hydrolysis of Formula V under acidic conditions affords hexahydronaphthalenones of Formula VI. Preferred hydrolytic conditions include a strong acid, such as hydrochloric or sulfuric acid, in an aqueous alcoholic medium, such as aqueous methanol or ethanol.

Ketone intermediates Formula VI are converted to corresponding octahydronaphthalenes, Formula XII, by reaction with ethanedithiol under acidic conditions to form corresponding dithiolanes, Formula XI, followed by reductive desulfuration. Preferred conditions for the dithiolane formation include borontrifluoride etherate in methanol. Preferred conditions for the desulfuration include Raney nickel in refluxing absolute ethanol. The side-chain hydroxyl group of Formula XII is replaced by iodine for subsequent reactions. A preferred method involves reaction of Formula XII with p-toluenesulfonyl chloride in pyridine, which forms an intermediate tosylate ester that can be converted to compound XIII by reaction in refluxing acetone with an alkali metal iodide, such as sodium or potassium iodide. The extended side-chain compound, Formula XV, is prepared from XIII by reaction with the lithium salt, Formula XIV, of a 2-(2,2-dialkoxyethyl)-1,3-dithiane, prepared according to the method of Seebach and Corey, *J. Org. Chem.*, 40, 231 (1975). A preferred compound XIV is 2-(2,2-dimethoxyethyl)-1,3-dithiane. The dithiane group of XV is removed to give corresponding ketones, Formula XVI. A preferred method for removing the dithiane group involves heating in aqueous acetone with cadmium carbonate and mercuric chloride, followed by treatment with potassium iodide.

Ketone intermediates XVI are reduced to the corresponding secondary alcohols, which are then silylated to form compounds of Formula XXI. Suitable reducing conditions include active metal hydrides, such as sodium borohydride (or boron-substituted derivatives thereof) and lithium aluminum hydride (or aluminum-substituted derivatives thereof). A preferred reducing procedure employs sodium borohydride in refluxing anhydrous ethanol. Suitable silylating conditions include hindered trialkylsilyl halides in dry unreactive organic solvents, using a base to scavenge liberated hydrogen chloride. A preferred silylating procedure employs t-butyldiphenylsilyl chloride in dimethylformamide in the presence of imidazole. Under acidic conditions, intermediates of Formula XXI are converted to aldehydes of Formula XXII. Suitable acidic conditions include solutions of formic acid in aqueous dioxane. Alkylation of XXII with alkyl acetate, under strongly basic conditions in an inert organic solvent, affords extended side-chain compounds of Formula XXIII. Preferred alkylating conditions include the method described above and illustrated in Chart A for converting I to II. Silyl-protected compounds XXIII are deblocked with suitable reagents, preferably tetrabutylammonium fluoride, and chromatographed preferably on silica gel to give compounds of Formula XXIV and XXV, the title compounds of this invention.

Some of the reactions described above form compounds having asymmetrically substituted carbon atoms. For those compounds having more than one asymmetric carbon center, partially or completely separated components may be obtained using separation methods, such as recrystallization and chromatography, known to those skilled in the art.

DESCRIPTION OF THE PREFERRED EMBODIMENT

The operation of this invention is further elaborated by the representative examples below.

EXAMPLE 1

Ethyl 1,2,3,4-tetrahydro-1-hydroxy-6-methoxy-1-naphthaleneacetate.

A solution of 1.41 g (19 mmoles) of isopropylmethylamine in 10 ml of tetrahydrofuran was cooled to $-78°$, and 6.6 ml 1.1 equiv $\sim 1.67$ M (11 mmoles) of n-butyllithium was added dropwise. After fifteen minutes at $-78°$, a solution of 0.88 g (10 mmoles) of ethyl acetate in 3 ml of tetrahydrofuran was added dropwise. After stirring for ten minutes at $-78°$ a solution of 1.76 g (10 mmoles) of 6-methoxy-1-tetralone in 5 ml of tetrahydrofuran was added. After ten minutes the mixture was acidified with 10% hydrochloric acid and concentrated to dryness. The residue was extracted into diethyl ether, and the organic phase was washed with brine, dried over magnesium sulfate, filtered and concentrated. The crude material was chromatographed on silica gel to give 2.4 g of the title compound as an oil. Structure assignment was confirmed by the proton nmr spectrum.

HNMR (CDCl$_3$): $\delta 1.25$ (t, J=7H$_2$, 3H); 1.6–2.2 (m, 3H), 2.5–2.9 (m, 3H), 3.78 (d, J=7H$_2$, 2H), 3.73 (S, 3H), 4.17 (q, J=7H$_z$, 2H), 6.5–7.7 (m, 3H).

IR, (CHCl$_3$) 1735 cm$^{-1}$.

EXAMPLE 2

Ethyl 1,2,3,4-tetrahydro-6-methoxy-1-naphthaleneacetate.

A solution of 0.95 g (3.5 mmole) of the product compound of Example 1 in 40 ml of ethanol was hydrogenated at 60° using 60 psi of hydrogen gas over 10% palladium on carbon catalyst. After filtration, the reaction mixture was concentrated to dryness. The crude material was chromatographed on silica gel to give 0.5 g of the title compound. Structure assignment was confirmed by the proton nmr spectrum.

$\delta 1.24$ (t, J=7Hz, 3H), 1.6–2.0 (m, 3H), 2.4–3.0 (m, 5H), 3.1–3.5 (m, 1H), 3.73 (S, 3H), 4.15 (q$_7$, 2H), 6.5–7.3 (m, 3H).

EXAMPLE 3

1,2,3,4-tetrahydro-6-methoxy-1-naphthaleneethanol.

A solution of 24 mg (0.6 mmole) of lithium aluminum hydride in 10 ml of diethyl ether was added dropwise to a solution of 250 mg (1 mmole) of the product compound of Example 2 in 10 ml of ether. The reaction mixture was stirred at room temperature for one hour and then heated to reflux for thirty minutes. After cooling the reaction, a 30% ethyl acetate in ether solution was added dropwise, followed by a saturated sodium bisulfite solution. The organic phase was washed with water until neutral, then dried over magnesium sulfate.

Removal of the solvent gave 250 mg of crude material, which was used in the next step without further purification. Structure assignment was confirmed by the proton nmr spectrum.

$\delta 1.5$–2.1 (m, 6H), 3.73 (t, 2H), 3.75 (S, 3H), 6.5–7.3 (m, 3H).

IR, (CHCl$_3$) 3600 cm$^{-1}$.

|   | 1602 cm$^{-1}$ | |
|---|---|---|
|   | Theory | Found |
| C | 75.69 | 74.94 |
| H | 8.79  | 8.76  |

EXAMPLE 4

1,2,3,4,5,8-hexahydro-6-methoxy-1-naphthaleneethanol.

A solution of 1 g (4.8 mmole) of the alcohol product from Example 3 in 15 ml of tetrahydrofuran and 15 ml of t-butyl alcohol was cooled to less than 0°, and 45 ml of distilled liquid ammonia was added. This was followed by the addition over a ten-minute period of 600 mg (86 mmole) of lithium. After three hours, methanol was added to the reaction mixture until the blue color disappeared, and the ammonia was then evaporated under a stream of nitrogen. The residue was dissolved in 5 ml of water, extracted with diethyl ether and acidified with 5% hydrochloric acid. The organic phase was washed with water, dried over magnesium sulfate, filtered, and concentrated to dryness. The residue was chromatographed on silica gel to give 1.26 g of the title compound, contaminated with t-butanol. Structure assignment was confirmed by the proton nmr spectrum.

$\delta 1.6$–2.4 (7H), 2.4–3.0 (m, 7H), 3.4–4.0 (m, 3H), 3.5 (S, 3H).

EXAMPLE 5

4,4a,5,6,7,8-hexahydro-5-(2-hydroxyethyl)-2(3H)-naphthalenone

A solution of 1.26 g of the crude product compound of Example 4 in 50 ml of methanol and 50 ml of 3N hydrochloric acid was heated at 60° for thirty minutes. After the solution was stirred at room temperature for one hour, 50 ml of water was added. The methanol was evaporated and the product was extracted into chloroform, which was washed with water, dried over magnesium sulfate, filtered and concentrated to dryness. The crude material was chromatographed on silica gel to give 0.74 g of the title compound.

Structure assignment was confirmed by the proton nmr spectrum.

$\delta 1$–2.6 ppm (m, 14H), 3.6–4.0 (m, 3H), 5.85 (m, 1H).
IR, (CHCl$_3$) 1670 cm$^{-1}$ 1620 (w), 3620 (s), 3640 (w).
U.V $\lambda_{max}$ 239 m$\mu$ (G 15,000).

EXAMPLE 6

1,2,3,4,6,7,8,8a-octahydro-1-naphthaleneethanol

A solution of 4 g (0.02 mole) of the compound of Example 5 and 3.5 g (0.037 mole) of ethanedithiol in 200 ml of methanol was cooled to 0° C., and a solution of 2.5 ml (0.02 mole) of borontrifluoride etherate in 20 ml of methanol was added dropwise. The reaction mixture was stirred at 0° for four hours, then 5 ml of sodium bicarbonate solution was added. The methanol was evaporated and the product was extracted into ether, which was then washed with water, dried over magnesium, sulfate, filtered and concentrated to dryness. The crude material was chromatographed on silica gel to give 4.5 g of the intermediate 4',4a', 5',6', 7',8'-hexahydrospiro [1,3-dithiolane-2,2'(3'H)-naphthalene]-5'-ethanol, an oil having the expected nmr spectrum.

A mixture of 350 mg (1.3 mmole) of the intermediate compound and 2.6 g of a slurry of W-2 Raney nickel in ethanol in an additional 26 ml of absolute ethanol was heated as reflux for sixteen hours. After the reaction mixture was cooled, the catalyst was filtered and the solvent was evaporated. The product was extracted into diethyl ether and dried over magnesium sulfate. Chromatography on silica gel afforded 220 mg of the title compound. Structure assignment was confirmed by the proton nmr specturm.

$\delta$ 0.8–2.6 (m, 16H), 3.4–4.0 (m, 3H), 5.39 (m, 1H).

|   | Theory | Found |
|---|--------|-------|
| C | 79.94  | 79.08 |
| H | 11.18  | 11.06 |

EXAMPLE 7

1,2,3,4,6,7,8,8a-octahydro-1-(2-iodoethyl) naphthalene

A solution of 350 mg (1.9 mmole) of the product compound of Example 6 in 1 ml of pyridine was cooled to 0°, and a solution of 400 mg (2.1 mmole) of p-toluenesulfonyl chloride (190.65) in 2 ml of pyridine was added dropwise. An additional 1 ml of pyridine was used as a rinse for the p-toluenesulfonyl chloride. The reaction mixture was stirred at 0° for 24 hours and extracted with ether. The organic phase was washed with cold 1% hydrochloric acid until the aqueous phase remained aicidic and, then washed three times with water, dried over magnesium sulfate, filtered, and concentrated to dryness. A 40% yield of the tosylate derivative, 1,2,3,4,6,7,8a-octahydro-1-naphthaleneethanol,4 methylbenzenesulfonate, having the expected nmr spectrum was obtained.

A solution of 700 mg (2.1 mmole) of the tosylate derivative and 1.8 g (12 mmole) of sodium iodide in 30 ml of acetone was heated on a steam bath for three hours. The reaction mixture was cooled to room temperature and the solvent was removed under a stream of nitrogen. The product was extracted into Skelly B, dried over magnesium sulfate, filtered and concentrated to dryness. Chromatography on silica gel afforded 600 mg of the title compound. Structure assignment was confirmed by the nmr spectrum.

EXAMPLE 8

2-(2,2-dimethoxyethyl)-2-[2-(1,2,3,4,5,6,8,8a-octahydro-1-naphthalenyl)ethyl]-1,2-dithiolane.

A solution of 2 g (9.6 mmole) of in 20 ml of tetrahydrofuran was cooled to −78° and 5 ml (10.6 mmole) of n-butyl lithium was added dropwise. The reaction mixture was stirred at 0° for three hours and recooled to −78°. A solution of 2.0 g (6.9 mmole) of the product compound of Example 7 in 5 ml of tetrahydrofuran was added dropwise over a five minute period. The reaction mixture was stirred at −78° for one hour and at −20° for two hours, then quenched with 15 ml of 5% aqueous hydrochloric acid and warmed to room temperature. The solvent was evaporated and the product was extracted into ether, dried over magnesium sulfate, filtered, and concentrated. The crude material was chromatographed on silica gel to give 1.5 g of the title compound. Structure assignment was confirmed by the proton nmr spectrum.

$\delta$ 0.6–2.4 (m, 22H), 2.6–3.0 (m, 4H), 3.36 (S, 6H) 4.64 (t, J=4 Hz, 1H), 5.44 (m, 1H).

EXAMPLE 9

1,1-dimethoxy-5-(1,2,3,4,6,7,8,8a-octahydro-1-naphthalenyl)-3-pentanone

A solution of 5.0 g (29 mmole) of cadmium carbonate and 5.0 g (18.4 mmole) of mercuric chloride in 125 ml of acetone and 25 ml of water was heated to 50°, and a solution of 1.8 g (4.9 mmole) of the product compound of Example 8 in 25 ml of acetone was added. The reaction mixture was heated at 50° for fifteen minutes and an additional 2.5 g (14.5 mmole) of cadmium carbonate was added. The mixture was heated at 50° an additional 30 minutes and 6.5 g (39 mmole) of potassium iodide was added. After stirring at room temperature for 30 minutes, the solvent was evaporated and the product was extracted into diethyl ether. The organic phase was washed with water, dried over magnesium sulfate, filtered, and evaporated to dryness. Chromatography of the crude material on silica gel afforded the title compound. Structure assignement was confirmed by the proton nmr spectrum.

$\delta$ 0.8–2.6 (m, 18H), 2.68 (d, J=5.5 Hz, 2H), 3.34 (S, 6H), 4.8 (t, J=5.5 Hz, 1H), 5.43 (m, 1H).

EXAMPLE 10:

[3,3-dimethoxy-1-[2-(1,2,3,4,6,7,8,8a-octahydro-1-naphthalenyl)ethyl]propoxy](1,1-dimethylethyl)diphenylsilane A mixture of 1.45 g of the product compound of Example 9 and 250 mg of sodium borohydride in 5 ml of ethanol was heated to reflux for thirty minutes and then stirred at room temperature for thirty minutes. The reaction mixture was cooled to 0° and a 10% aqueous acetic acid solution was added dropwise until no further reaction occurred. The solution was made basic with sodium bicarbonate solution and the ethanol was evaporated. The intermediate product α-(2,2-dimethoxyethyl)-1,2,3,4,6,7,8,8a-octahydro-1-naphthalenepropanol was extracted into diethyl ether, and the organic phase was washed with water, dried over magnesium sulfate, filtered, and concentrated to dryness. The intermediate product, without further purification, was dissolved in 4 ml of dimethylformamide and 1.5 g of t-butyldiphenylsilyl chloride was added. The reaction mixture was cooled to 0° and 350 mg of imidazole was added. After stirring at room temperature for five hours, the reaction mixture was extracted with ether, washed with water, dried over magnesium sulfate, filtered, and concentrated to dryness. Chromatography on silica gel afforded 1.4 g of the title compound. Structure assignment was confirmed by the nmr spectrum.

$\delta$ 0.6–2.4 (m, 18H),
3.16 (S, 1H),
3.6–4.3 (m, 1H),
4.4–4.6 (m, 1H),
5.36 (m, 1H),
7.2–8.0 (m, 10H).

EXAMPLE 11

Ethyl δ[[1,1-dimethylethyl)diphenylsilyl]oxy]-1,2,3,4,6,7,8,8a-octahydro--hydroxy-1-naphthaleneheptanoate A solution of 1.5 g (2.9 mmole) of the product compound of Example 10 in 1.5 ml of dioxane was cooled to 10°, and a mixture of 15 ml of formic acid, 1.25 ml of water and 1.25 ml dioxane was added dropwise. The reaction mixture was stirred at room temperature for ninety minutes, then 30 ml of diethyl ether was added. The reaction mixture was made basic with saturated aqueous sodium bicarbonate, and then washed with water until neutral, dried over magnesium sulfate, filtered, and concentrated to give 1.3 g of the crude aldehyde intermediate, δ-[[(1,1-dimethylethyl)diphenylsilyl]oxy]-1,2,3,4,6,7,8,8a-octahydro-1-naphthalenepentanal.

A solution of 424 mg (3 mmole) of cyclohexyl isopropylamine in 50 ml of tetrahydrofuran was cooled to −78°, and 1.3 ml (5.2 mmoles) of n-butyllithium was added dropwise. After stirring the reaction mixture for fifteen minutes at −78°, a solution of 270 mg (3 mmole) of ethyl acetate in 25 ml of tetrahydrofuran was added dropwise. The reaction mixture was stirred at −78° for an additional thirty minutes and a solution of 1.3 g (2.8 mmole) of the aldehyde intermediate (prepared above) in 10 ml of tetrahydrofuran was added. After thirty minutes of stirring at −20°, the reaction mixture was neutralized with 5% aqueous hydrochloric acid. The solvent was removed and the product extracted into ether. The organic phase was washed with water, dried over magnesium sulfate, filtered, and concentrated to dryness. Chromatography on silica gel gave the title compound as two separate components which were identical by proton nmr spectrum except for the chemical shift of the methine proton adjacent to the silyloxy group. Isomer A weighed 0.68 and isomer B weighed 0.58 g.

δ0.8–2.6 (m, 36H), 3.2–3.45 (m, 1H), 4.0–4.2 (m, 3H), 5.2–5.4 (m, 1H), 7.2–8.0 (m, 10H).

EXAMPLE 12

Ethyl 1,2,3,4,6,7,8,8a-octahydro-β,δ-dihydroxy-1-naphthaleneheptanoate, component A, and tetrahydro-4-hydroxy-6-[(1,2,3,4,6,7,8,8a-octahydro-1-naphthalenyl)ethyl]2H-pyran-2-one, component A.

A solution of 0.68 g (1.2 mmole) of component A from Example 11 in 25 ml of tetrahydrofuran was treated dropwise with 2 ml (2 mmoles) of a 1M solution of tetrabutylammonium fluoride in tetrahydrofuran. The reaction mixture was stirred for two hours, after which 5 ml of water was added. The solvent was evaporated and the product extracted into diethyl ether. The organic phase was dried over magnesium sulfate, filtered, and concentrated to dryness. The crude material was chromatographed several times on silica gel to give 120 mg ethyl 1,2,3,4,6,7,8,8a-octahydro-β,δ-dihydroxy-1-naphthaleneheptanoate, of the open chain form of the product as an oil and 100 mg tetrahydro-4-hydroxy-6-[(1,2,3,4,6,7,8,8a-octahydro-1-naphthalenyl)ethyl]-2H-pyran-2one, of the lactone form of the product as a white solid. The lactone product was recrystallized from Skelly B to afford 80 mg of compound. Structure assignments were confirmed by proton nmr spectra and by elemental analyses.

|   | SC-35671 (lactone) | | δ0.8–2.3 (m, 23H) |
|---|---|---|---|
|   | Theory | Found | 2.5 (d7, J-6.5 Hz, 2H) |
| C | 73.35 | 72.67 | 3.8–4.1 (m, 2H) |
| H | 9.41 | 9.51 | 4.37 (q, 2H) |
|   |   |   | 5.42 (m, 1H) |

SC-39718

δ0.75–2.5 (m, 20H), 2.5–2.8 (m, 2H), 2.38 (m, 1H), 2.65 (m, 1H), 5.75 (m, 1H).

EXAMPLE 13

Ethyl 1,2,3,4,6,7,8,8a-octahydro-β,δ-dihydroxy-1-naphthaleneheptanoate, component B, and tetrahydro-4-hydroxy-6-[(1,2,3,4,6,7,8,8a-octahydro-1-naphthalenyl)ethyl]-2H-pyran-2-one, component B.

The silyl group was removed from 550 mg (0.98 mmoles) of component B of Ex. 11 in the same manner as for component A (see Ex. 12). Chromatography on silica gel ethyl 1,2,3,4,6,7,8,8a-octahydro-β,δ-dihydroxy-1-naphthalene-heptanoate, afforded 220 mg of the open chain form of the product and tetrahydro-4-hydroxy-6-[(1,2,3,4,6,7,8,8a-octahydro-1-naphthalenyl)ethyl]-2H-pyran-2-one, 42 mg of the lactone form of the product. Structure assignments were confirmed by proton nmr spectra and by elemental analyses.

Open Chain Compound

|   | Theory | Found |
|---|---|---|
| C | 70.34 | 69.75 |
| H | 9.94 | 9.77 |

SC-35678
δ0.75–2.5 (m, 20H)
2.5–2.8 (m, 2H)
2.38 (m, 1H)
2.65 (, 1H)
5.75 (m, 1H)

IR 3620 cm$^{-1}$
2800–3050 cm$^{-1}$
1730 cm$^{-1}$

SC-35739
δ0.8–2.3 (m, 23H)
2.5 (d, J=6.5 Hz, 2H)
3.8–4.1 (m, 2H)
4.37 (1, 2H)
5.42 (m, 1H)

CHART A

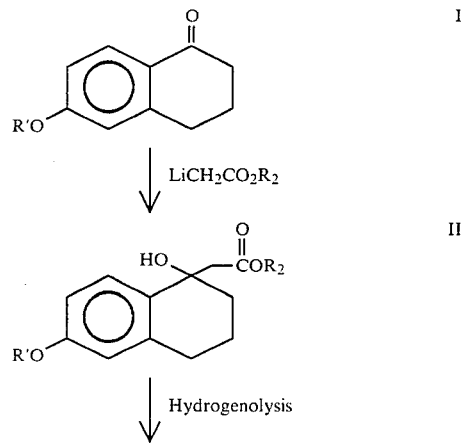

CHART A -continued
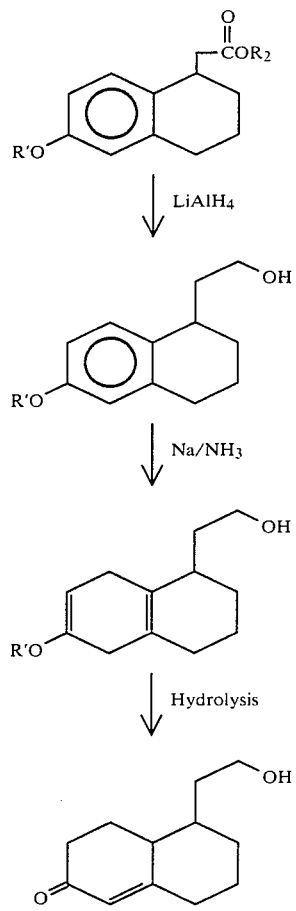
CHART B
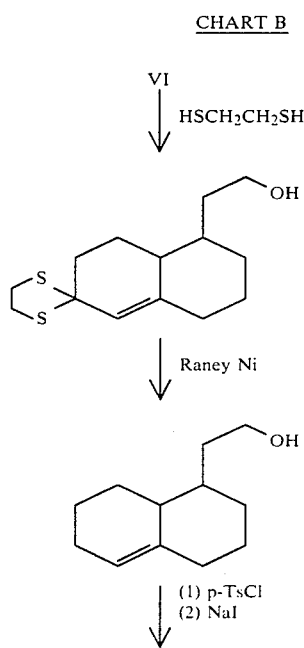
CHART B -continued
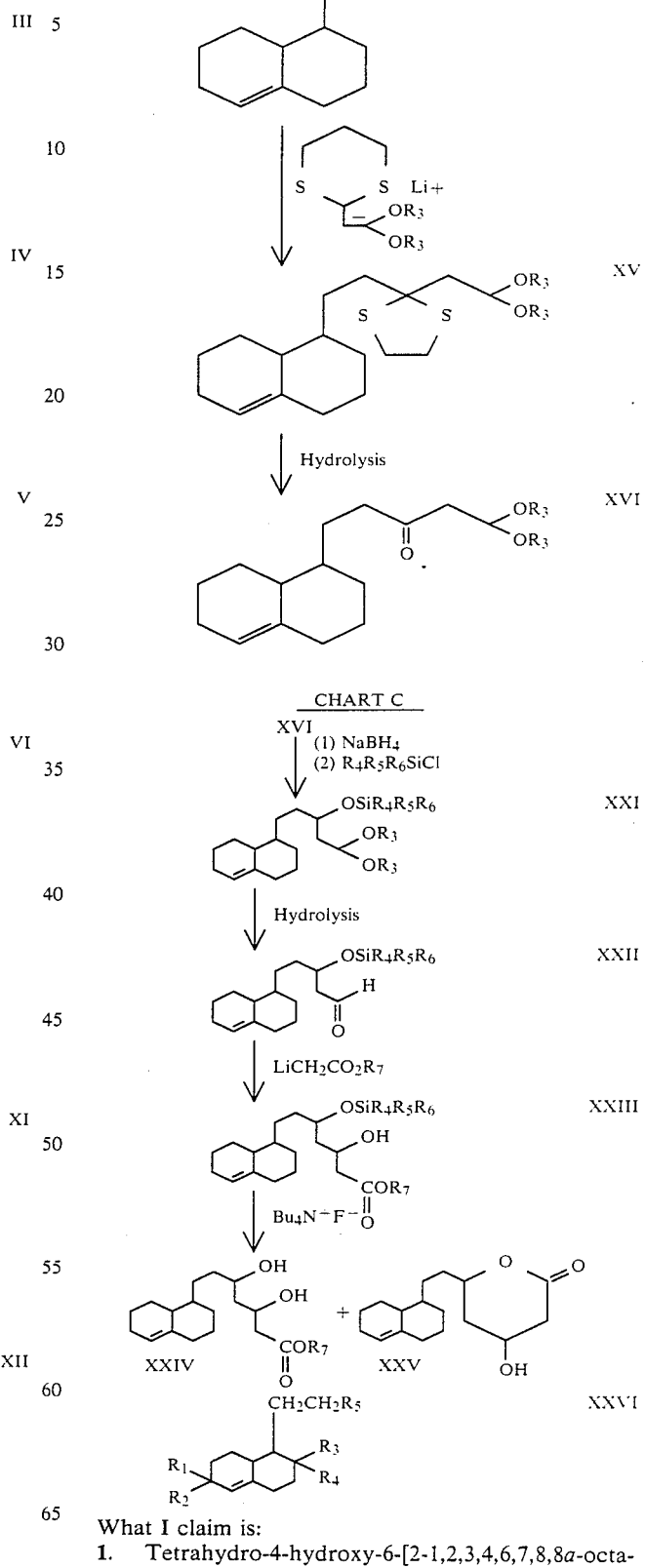
What I claim is:
1. Tetrahydro-4-hydroxy-6-[2-1,2,3,4,6,7,8,8a-octahydro-1-naphthalene)ethyl]-2H-pyran-2-one.
* * * * *